(12) United States Patent
Funahashi

(10) Patent No.: US 6,820,100 B2
(45) Date of Patent: Nov. 16, 2004

(54) IMAGE MANAGEMENT SYSTEM AND IMAGE MANAGEMENT METHOD

(75) Inventor: Takeshi Funahashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 123 days.

(21) Appl. No.: 09/965,852

(22) Filed: Oct. 1, 2001

(65) Prior Publication Data

US 2002/0081039 A1 Jun. 27, 2002

(30) Foreign Application Priority Data

Sep. 29, 2000 (JP) ........................................ 2000-299075

(51) Int. Cl.[7] ............................................. G06F 17/30
(52) U.S. Cl. .................................... 707/204; 707/104.1
(58) Field of Search ............................ 707/2, 10, 100, 707/204, 104.1; 378/4, 9; 382/132; 600/301, 407; 711/161

(56) References Cited

U.S. PATENT DOCUMENTS 6,349,373 B2 * 2/2002 Sitka et al. ................. 711/161
6,574,629 B1 * 6/2003 Cook, Jr. et al. ............. 707/10
6,574,742 B1 * 6/2003 Jamroga et al. ............ 713/400

* cited by examiner

Primary Examiner—Diane D. Mizrahi
Assistant Examiner—Apu Mofiz
(74) Attorney, Agent, or Firm—Sughrue Mion, PLLC

(57) ABSTRACT

The present invention provides an image management system and image management method for automatically retaining necessary diagnostic image files without relying on manual operations and thereby averting the risk of involuntary data deletion. An image file server connected to modality apparatuses and image viewers permanently archives diagnostic images with a record indication attached automatically on a removable medium. It also displays the image once, and if there is no user indication within a certain period of time after displaying, then it permanently archives the diagnostic image automatically. Alternatively, the diagnostic image may be temporarily stored once with a reservation for permanent archiving, then after a certain period of time it may be permanently archived automatically. When no removable medium is loaded, a reservation may be made for permanent archiving.

11 Claims, 12 Drawing Sheets

IMAGE MANAGEMENT SYSTEM AND IMAGE MANAGEMENT METHOD

FIELD OF THE INVENTION

The present invention relates to an image management system and image management method for managing image data by way of a network, and in particular to an image management system and image management method for managing diagnostic image taking apparatuses, such as a CT (Computer Tomography) apparatus, MR (Magntic Resonance) apparatus and CR (Computed Radiography) apparatus, by way of a network.

More specifically, the present invention relates to an image management system and image management method for retaining and managing diagnostic image data transferred over a network, and in particular to an image management system and image managemenet method for automatically retaing necessary diagnostic image files without relying on manual operations and thereby averting the risk of involuntary data deletion.

BACKGROUND OF THE INVENTION

Along with the progress of information processing technologies in recent years, general-purpose computer systems with sophisticated and powerful computing capabilities have become widely used in various research organizations and offices of a company and even in common homes. Applicable fields of computers have also expanded, wherein not only computer data but also various kinds of media data such as images (including both static and moving images) and voices have been handled on a computer as digitized files.

For example, in the fields of medical and diagnostic technologies, patients are diagnosed their symptoms based on fluoroscopic images or cross-sectional images of their bodies, which are taken by various modality apparatuses such as a CT (Computed Tomography) apparatus, MR (Magnetic Resonance) apparatus, and CR (Computed Radiography) apparatus.

Conventionally, diagnostic images of patient bodies taken by these kinds of modality apparatuses have only been directly printed out to sensitive films by an image output apparatus that is installed near the modality apparatus. Accordingly, managing the diagnostic images afterward is performed by manually sorting and arranging the films as physical media, thus it requires a significant man power to move, distribute and share the diagnostic images, thereby leading to inefficient works.

On the contrary, recently diagnostic images taken by modality apparatuses are digitized by a image reader and managed by a computer as image files. Furthermore, by interconnecting modality apparatuses in a hospital and computers used by doctors and nurses via a network laid in the hospital, medical and diagnostic information such as diagnostic images and medical charts can be treated transparently on the network space. Namely, it becomes possible to transfer the diagnostic images to a remote terminal and share the medical and diagnostic information among each of the terminals.

For example, diagnostic image files taken by a radiographer using a modality apparatus, and also verified afterward, are once stored in an image storage server on a network. A doctor who needs a diagnostic image (i.e., radiogram-reading doctor) can access the image storage server from his desk, retrieve the diagnostic image, and further transfer the diagnostic image along with the diagnostic results to the image storage server. Accordingly, the diagnostic data of a number of patients can be managed in a lump in the hospital. Moreover, a doctor can retrieve later the diagnostic image that he observed once from the image storage server and determine a healing condition in time series by comparing it with the latest one. Medical records such as diagnostic images and diagnostic results are obliged, or recommended, to be saved at medical institutions for a given period of time.

In addition, providing a print server on the network allows sharing of an expensive printer for film printing among multiple modality apparatuses. Namely, technicians and doctors can transfer image files taken by the modality apparatuses and image files stored on the image storage server to the remote print server to print them out on the films.

Furthermore, it is also possible to install on the network the workstations (WS) for viewing diagnostic images, that is, image viewers, in addition to the modality apparatuses. Doctors can observe and diagnose the diagnostic images taken by the modality apparatuses on the image viewer. For observation, the image processing conditions applied to the diagnostic images may be changed or corrected by the doctor.

By the way, in a hospital (in particular a large-scaled general hospital), a number of modality apparatuses are installed as supply sources of diagnostic images. On each of the modality apparatuses, radiographic technicians who operate the modality apparatuses (e.g., radiographers) take photographs of affected parts or entire bodies of patients or investigate the taken images and then send image data to the image storage server one after another. Doctors retrieve diagnostic image data from the image storage server via the network for observation and diagnosis, thereafter they store it in the image storage server as image files with diagnostic results appended. In other words, the image storage server stores a large number of the image files to which plural file operators perform various operations.

The image storage server generally comprises a huge hard disk drive, which temporarily stores vast amounts of image files sent from the computers that are used in conjunction with modality apparatuses or by doctors. However, as a result of endless medical practices, the total capacity of the image files to be retained as medical records may exceed the storage capacity of the hard disk at a relatively early stage.

If further diagnostic image files are sent even after the storage capacity is exceeded, a storage area for new files must be secured by discarding old files. As a result, involuntary data deletion may occur, wherein the medical records obliged, or recommended, to be retained are deleted.

In view of such fact, the image files temporarily stored on the hard disk drive are moved to removable media such as a DVD (Digital versatile Disc) or MO (Magnetic-optical Disc), in order to permanently retain the medical records. Though one removable medium naturally has its limit of storage capacity, image files can be permanently retained nearly without limitation by replacing or supplementing a medium loaded in the media drive.

However, conventionally, moving medical records to the removable media are performed manually, which causes the increase of costs. In addition, as manual operations of image storage may be complex or get into a mess in a situation where many people work at each place on the network, important image data might be lost by mistake or, to the contrary, unimportant image data might be retained permanently, thereby leading to waste.

The present invention is directed to provide a great image management system and image management method for appropriately managing diagnostic image data output by various kinds of medical diagnostic image taking apparatuses, such as a CT (Computed Tomography) apparatus, MR (Magnetic Resonance) apparatus and CR (Computed Radiography) apparatus, by way of a network.

The present invention is also directed to provide a great image management system and image management method for automatically retaining necessary diagnostic image files without relying on manual operations and averting the risk of involuntary data deletion.

SUMMARY OF THE INVENTION

In view of the above problems, in a first aspect of the present invention, there is provided an image management system for managing image files on a network, comprising: network interface transmitting and receiving the image files via the network; a first image storage temporarily storing the image files; a second image storage permanently archiving the image files; and a controller controlling storage operations of the image files received via the network, wherein in response to receipt of the image file with a record indication attached, the controller stores the image file in either the first or second image storage in accordance with the record indication.

With the image management system according to the first aspect of the invention, in response to the record indication from a sender of the image files, the image files are permanently archived automatically, thus averting the risk of deleting important diagnostic images due to inattention or memory loss as well as saving the operators the trouble of storage operations.

In a second aspect of the invention, there is provided an image management system for managing image files on a network, comprising: a network interface transmitting and receiving the image files via the network; first image storage temporarily storing the image files; second image storage permanently archiving the image files; an image display displaying the image files; user input device inputting an indication from a user; and controller controlling storage operations of the image files received via the network, wherein in response to that no indication has been made by the user for a certain period of time since the image file was displayed on the image display, the controller archives the image file permanently in the second image storage.

With the image management system according to the second aspect of the invention, as the image file is to be permanently archived automatically after a certain period time has passed since it was displayed, it is possible to avert the risk of users deleting diagnostic images because of neglecting storage operations due to inattention or memory loss, as well as to save the operators the trouble of storage operations. For example, since the diagnostic image observed by a doctor is permanently archived automatically after a certain period of time has passed since it was displayed on the image viewer for observation, the integrity of medical records is suitably maintained.

In a third aspect of the invention, there is provided an image management system for managing image files on a network, comprising: a network interface transmitting and receiving the image files via the network; a first image storage temporarily storing the image files; a second image storage permanently archiving the image files; and a controller controlling storage operations of the image files received via the network, wherein the controller temporarily stores the image file with permanent archiving indicated in the first storage in a condition where a reservation for permanent archiving is made, as well as permanently archives the image file in the second image storage after a certain period time has passed.

With the image management system according to the third aspect of the invention, for image files for which permanent archiving is reserved, they are to be permanently archived automatically after a certain period time has passed without an indication from a user, thus it is possible to avert the risk of the user deleting diagnostic images due to inattention or memory loss as well as to save the operators the trouble of storage operations.

In a fourth aspect of the invention, there is provided an image management system for managing image files on a network, comprising: a network interface transmitting and receiving the image files via the network; a first image storage temporarily storing the image files; a second image storage permanently archiving the image files on a removable medium; and a controller controlling storage operations of the image files received via the network, wherein in response to a fact that no removable medium is loaded in the second image storage or an enough free capacity does not exist in the removable medium currently loaded just when an indication is made to permanently archive the image file, the controller temporarily stores the image file in the first image storage in a condition where a reservation for permanent archiving is made.

With the image management system according to the fourth aspect of the invention, as the image file is temporarily stored on a hard disk or the like automatically when the removable medium for permanent archiving does not exist, it is possible to avert the risk of the user deleting important diagnostic images due to inattention or memory loss as well as to save the operators the trouble of storage operations.

In a fifth aspect of the invention, there is provided an image management system for managing image files on a network, comprising: a network interface transmitting and receiving the image files via the network; a first image storage temporarily storing the image files; a second image storage permanently archiving the image files; and a controller controlling storage operations of the image files received via the network, wherein upon termination of the system the controller determines whether the image file with permanent archiving reserved is temporarily stored in the first image storage, and if the determination is affirmative, querying a user whether or not to archive the file permanently and then performing any processing in accordance with a user indication responsive to the query before terminating the system.

If the system is terminated while the image file with permanent archiving reserved remains, a user might forget the existence of the unsaved file afterward, resulting in involuntary data deletion. Furthermore, if the system is terminated after the image file with permanent archiving reserved is permanently archived, the termination processing might be inappropriately lengthened. With the image management system according to the fifth aspect of the invention, upon termination of the system, it is determined whether the image file with permanent archiving reserved is stored temporarily, and if the determination is affirmative, querying a user whether or not to archive it permanently and then performing any processing in accordance with a user indication responsive to the query, whereby the user can select either data integrity or time reduction for termination processing which he prefers.

In a sixth aspect of the invention, there is provided an image management system for managing image files on a network, comprising: a network interface transmitting and receiving the image files via the network; a first image storage temporarily storing the image files; a second image storage permanently archiving the image files on a removable medium; and a controller controlling storage operations of the image files received via the network, wherein in response to a fact that the removable medium is not loaded in the second image storage or an enough free capacity does not exist in the removable medium currently loaded just when an indication is made to permanently archive the image file, the controller temporarily stores the image file in the first image storage in a condition where a reservation for permanent archiving is made, and thereafter in response to loading of a new removable medium into the second image storage, permanently archiving the image file on the removable medium.

With the image management system according to the sixth aspect of the invention, as the image file is temporarily stored on a hard disk or the like automatically when the removable medium for permanent archiving does not exist, and further the image file with permanent archiving reserved is permanently archived automatically when a new removable medium is loaded, it is possible to avert the risk of a user accidentally deleting important diagnostic images due to inattention or memory loss as well as to save the operators the trouble of storage operations.

In a seventh aspect of the present invention, there is provided an image management method for managing image files on a network, comprising the steps of: receiving the image file with a record indication attached via the network; and either temporarily storing or permanently archiving the image file in accordance with the record indication.

With the image management method according to the seventh aspect of the invention, in response to the record indication from a sender of the image files, the image files are permanently archived automatically, thus averting the risk of deleting important diagnostic images due to inattention or memory loss as well as saving the operators the trouble of storage operations.

In an eighth aspect of the invention, there is provided an image management method for managing image files on a network, comprising the steps of: receiving the image file with a record indication attached via the network; displaying the image file received; waiting for an input of record indication from a user after displaying the image file; and archiving the image file permanently in response to that no indication has been made by the user for a certain period of time since the image file was displayed.

With the image management method according to the eighth aspect of the invention, as the image file is to be permanently archived automatically after a certain period time has passed since it was displayed, it is possible to avert the risk of users deleting diagnostic images due to inattention or memory loss as well as to save the operators the trouble of storage operations. For example, since the diagnostic image observed by a doctor is permanently archived automatically after a certain period of time has passed since it was displayed on the image viewer for observation, the integrity of medical records is suitably maintained.

In a ninth aspect of the invention, there is provided an image management method for managing image files on a network, comprising the steps of: receiving the image file with a record indication attached via the network; temporarily storing the image file with permanent archiving indicated in a condition where a reservation for permanent archiving is made; and permanently archiving the image file after a certain period time has passed since the reservation was made.

With the image management method according to the ninth aspect of the invention, for image files for which permanent archiving is reserved, they are to be permanently archived automatically after a certain period time has passed without an indication from a user, thus it is possible to avert the risk of the user deleting diagnostic images due to inattention or memory loss as well as to save the operators the trouble of storage operations.

In a tenth aspect of the invention, there is provided an image management method for managing image files on a network, comprising the steps of: receiving the image file with a record indication attached via the network; determining whether a removable medium for permanent archiving exists in response to the record indication of permanent archiving; and temporarily storing the image file in a condition where a reservation for permanent archiving is made in response to the absence of the removable medium.

With the image management method according to the tenth aspect of the invention, as the image file is temporarily stored on a hard disk or the like automatically when the removable medium for permanent archiving does not exist, it is possible to avert the risk of the user deleting important diagnostic images due to inattention or memory loss as well as to save the operators the trouble of storage operations.

In an eleventh aspect of the invention, there is provided an image management method for managing image files on a network, comprising the steps of: receiving the image file with a record indication attached via the network; determining upon termination of the system whether the image file with permanent archiving reserved is temporarily stored; if the determination is affirmative, querying a user whether or not to archive the file permanently; and performing any processing in accordance with a user indication responsive to the query before terminating the system.

If the system is terminated while the image file with permanent archiving reserved remains, a user might forget the existence of the unsaved file afterward, thereby resulting in involuntary data deletion. Furthermore, if the system is terminated after the image file with permanent archiving reserved is permanently archived, the termination processing might be inappropriately lengthened. With the image management system according to the eleventh aspect of the invention, upon termination of the system, it is determined whether the image file with permanent archiving reserved is stored temporarily, and if the determination is affirmative, querying a user whether or not to archive it permanently and then performing any processing in accordance with a user indication responsive to the query, whereby the user can select either data integrity or time reduction for termination processing which he prefers.

In a twelfth aspect of the invention, there is provided an image management method for managing image files on a network, comprising the steps of: receiving the image file with a record indication attached via the network; determining whether a removable medium for permanent archiving exists in response to the record indication of permanent archiving; temporarily storing the image file in a condition where a reservation for permanent archiving is made in response to the absence of the removable medium; and in response to loading of a new removable medium, permanently archiving the image file with permanent archiving reserved on the removable medium.

With the image management method according to the twelfth aspect of the invention, as the image file is temporarily stored on a hard disk or the like automatically when the removable medium for permanent archiving does not exist, and further the image file with permanent archiving reserved is permanently archived automatically when a new removable medium is loaded, it is possible to avert the risk of a user accidentally deleting important diagnostic images due to inattention or memory loss as well as to save the operators the trouble of storage operations.

Other purposes, features and advantages of the present invention will be appreciated from the following detailed description of the embodiments of the invention in conjunction with the accompanying drawings.

DETAILED DESCRIPTION OF PREFERRED EMBODIMENTS

Now an embodiment of the present invention will be described with reference to the drawings.

Figure 1:
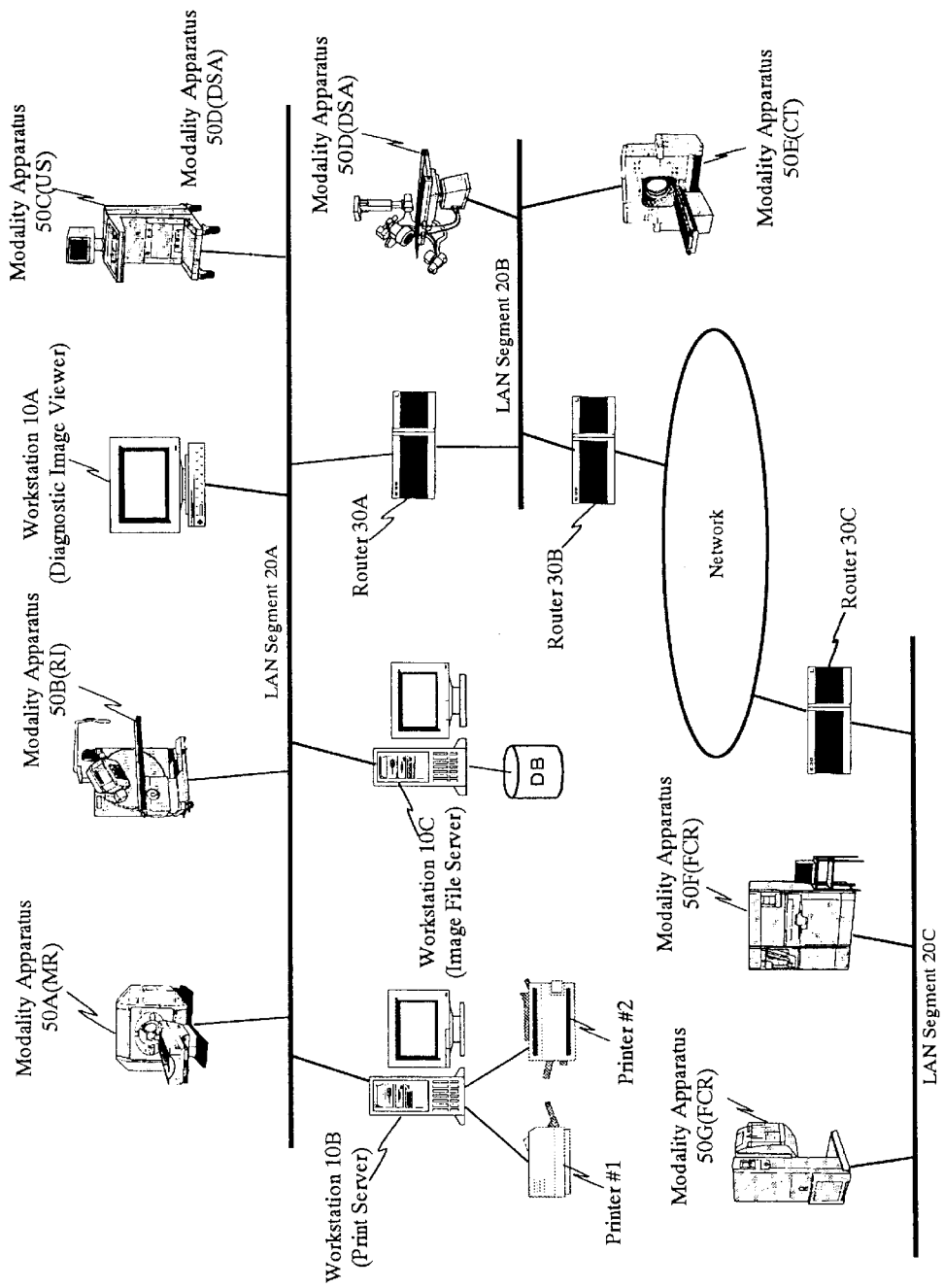
FIG. 1 depicts a schematic diagram of a network system sharing medical diagnostic image files among multiple terminals.

FIG. 1 depicts a schematic diagram of a network system sharing medical diagnostic image files among multiple terminals. On the network system, medical diagnostic images taken by multiple modality apparatuses 50A, 50B, etc., can be handled through each of workstations 10A, 10B, etc. Each of the modality apparatuses and each of the workstations that can electrically handle the diagnostic images are generally connected to the network using the network interface card (NIC) (not shown).

In FIG. 1, the network may be a LAN (Local Area Network) provided within a single hospital, for example. The LAN may be constructed by a single LAN segment 20 or by multiple LAN segments that are interconnected via routers (or gateways) 30. Alternatively, the network may be a WAN (Wide Area Network) that is constructed by connecting LANs each other located at remote hospitals via a dedicated line or may be a WAN like the Internet.

Connected to the network are multiple modality apparatuses serving as supply sources of medical images, including a MR (Magnetic Resonance) apparatus 50A, RI apparatus 50B, US apparatus 50C, DSA (Digital Subtraction Angiography) apparatus 50D, CT (Computed Tomography) apparatus 50E, CR (Computed Radiography) apparatus 50F, etc., and workstations 10A, 10B, etc.

Generally, each of the modality apparatuses 50 is located in a dedicated diagnostic room (not shown) in a hospital. Furthermore, specialized technicians such as radiographers are deployed to each of the modality apparatuses 50, who take photographs of affected parts or entire bodies of patients or inspect the taken images or may possibly photograph again.

A computer system shown by a reference number 10B operates as a print server. Connected to print server 10B are, for example, two printers locally via adapter cards (not shown).

Print server 10B performs to the image data sent from each of the modality apparatuses 50 on the network the format operation (such as a layout operation on a film with a predetermined size), enlargement or reduction operation of images, and gradation conversion suitable for diagnosis, etc., before printout.

A printer for medical diagnostic images is typically a type of that which forms an image on a sensitive film rather than plain paper. The reason for using a film rather than plain paper as an output medium depends on the high resolution of the film compared with plain paper (particularly a dynamic range is wide), which allows the correct observation of the affected parts based on the output images.

A workstation (WS) shown by a reference number 10C operates as a file server, which comprises a mass storage device for storing a huge amount of diagnostic image files.

A further workstation (WS) shown by a reference number 10A operates as an diagnostic image viewer. The image viewer 10A is manipulated by a doctor, who retrieves a plurality of past diagnostic images from file server 10B and checks the process of recovery or the evolution of the disease on the display screen. The image viewer 10A typically comprises a high-resolution CRT (Cathode Ray Tube) display with a large screen. The description about diagnostic results by a doctor is saved in the image file server 10C along with the corresponding diagnostic image files.

Each of the workstations 10 and modality apparatuses 50 on the network is connected transparently according to a predetermined communication protocol. For example, in the case of OSI (Open Systems Interconnection) reference standard model, a physical layer and data link layer of the network are constructed by the Ethernet, while a transport layer and network layer are constructed by the TCP/IP (Transmission Control Protocol/Internet Protocol). Upper layers higher than a session layer inclusive are provided as specialized protocols given by a plurality of the manufacturers of medical products.

One of the representative upper layers of protocol in the medical industry is DICOM (Digital Imaging and Communication for Machine). DICOM is the industrial standard specifying the transfer of images and other medical information between computers, which allows the digital communication between a diagnostic apparatus and a therapeutic apparatus produced by different manufacturers.

Using the network system for medical images as shown in FIG. 1, every medical image data acquired in a hospital is digitized and thereafter moved, transferred, distributed or shared among multiple terminals on the network. Namely, diagnostic data obtained in a diagnostic room is also available to a computer provided in another diagnostic room (or a diagnostic room in a remote/another hospital). It is also possible to check the process of recovery or the evolution of the disease by retrieving the past diagnostic images from the image file server 10C as needed. Furthermore, computer resources, such as an expensive film printer for outputting images taken by the modality apparatuses 50 and images retrieved from the image file server 10C, are shared among multiple modality apparatuses and workstations.

Figure 12:
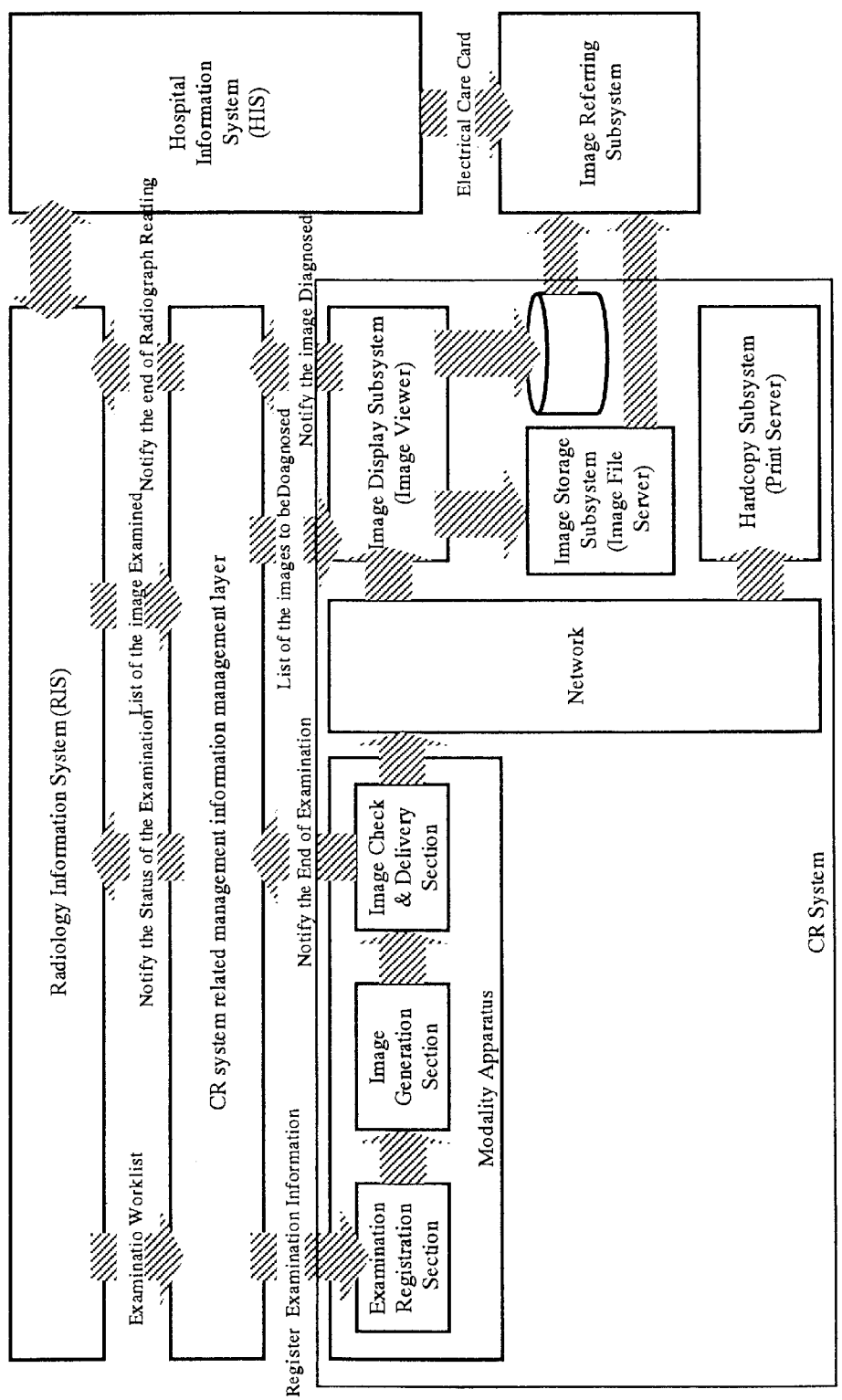
FIG. 12 depicts a functional block diagram for managing diagnostic images digitized by a network system for medical images.

Using the network structure shown in FIG. 1, diagnostic images are digitized, that is, computerized and managed and shared in the network for the purpose of diagnostic operations. FIG. 12 depicts a functional block diagram for managing diagnostic images digitized by a network system for medical images. The system shown in FIG. 12 comprises a RIS (Radiology Information System), a CR system related management information management layer, and a CR system.

The radiology information system totally manages the diagnostic images dealt with by the department of radiology in a hospital and other information. Generally, the department of radiology has one or more modality apparatus such a CR, wherein each of the modality apparatuses is located in a dedicated photographic room (not shown).

The CR system related information management layer constructs a database composed of RIS information and CR system information and performs various kinds of processing ranging from generation to utilization of diagnostic images using this database as well as notifies the status of the examination to the upper radiology information system.

The CR system that exchanges data with the CR system related information management layer comprises a modality apparatus, an image display subsystem, an image storage subsystem, and a hard copy subsystem. The image display subsystem is embodied by an image viewer 10A, the image storage subsystem is embodied by an image file server 10C, and the hard copy subsystem is embodied by a print server 10B and film printer.

The modality apparatus comprises an examination registration section, an image generation section, and an image check and delivery section, those of which perform registration, image generation, image check and delivery, and notification of the end of the examination of photographed image information in response to an examination request.

The radiology information system has an interface with a hospital information system (HIS), which totally manages medical information in the hospital, and receives examination requests at the department of radiology or feeds back the examination results.

The CR system related information management layer acquires an examination work list from the radiology information system and registers the examination information with the modality apparatus.

The modality apparatus is used by a radiographer to generate diagnostic images of patients according to the examination information registered as well as notify the CR system related information management layer of the end of the examination. The diagnostic images checked at the modality apparatus may be transferred to the image display subsystem or hard copy subsystem via the network.

In response to the notification of the end of the examination from the modality apparatus, the CR system related information management layer notifies the radiology information system of the status of the examination. Furthermore, receiving from the radiology information system a list of images for which the examination has ended, the CR system related information management layer creates a list of images that can be diagnosed and sends this list to the image display subsystem.

Based on the list of images that can be diagnosed, the image display subsystem is used by a doctor to diagnose the diagnostic images. Then the image display subsystem returns notification of the end of the observation to the CR system related information management layer, and in turn the latter returns notification of the end of the observation to the radiology information system. The diagnostic images observed may be transferred to the image storage subsystem or hard copy subsystem, etc.

The image display subsystem is also used by a doctor in order to create and store a medical reporting document which is related to the diagnostic results. The image referring subsystem further refers to the diagnostic results of the image display subsystem and the diagnostic images saved in the image storage subsystem, and then integrates those kinds of information into a electrical care card sent from the Hospital information system (HIS).

Figure 2:
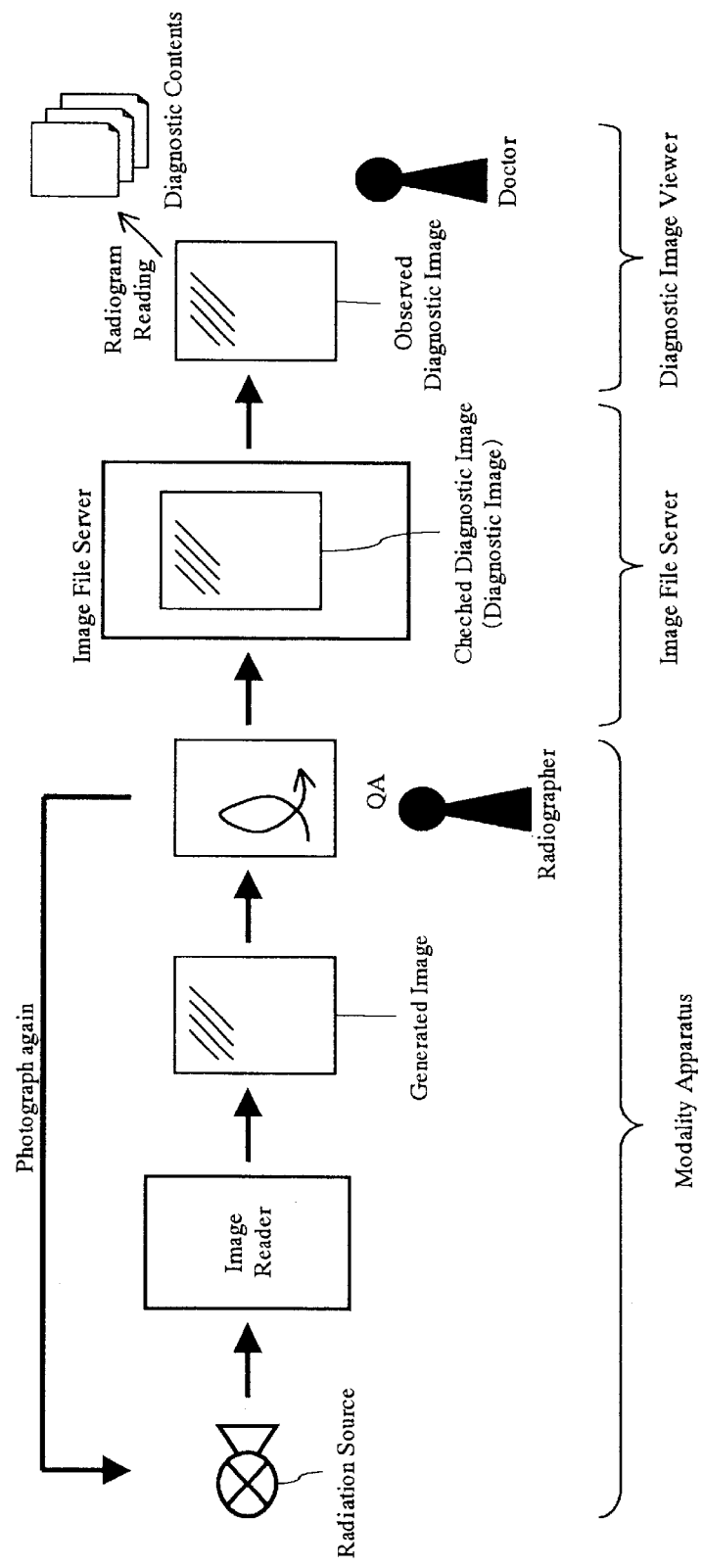
FIG. 2 depicts a flow of diagnostic image files dealt with by a network system for medical images according to a flow of medical and diagnostic affairs.

FIG. 2 depicts a flow of diagnostic image files dealt with by a network system for medical images according to a flow of medical and diagnostic affairs.

A technician (Radiographer) who operates a modality apparatus using a radiation irradiated from a radiation source, takes photographs of affected parts or entire bodies of patients and then scans the taken image using a image reader to obtain a "generated image" in a digital format.

Next, the technician determines on an image check apparatus whether the generated image is in sufficient quality for a doctor to diagnose (Radiographic Reading). One of the image check operations is called QA (Quality Assurance). A set of a radiation source, radiogram reader and image checker constitutes a modality apparatus.

In the process of QA, a radiographer may adjust image processing parameters such as the one for dark and light adjustment of the taken image, nevertheless, if the image with sufficient quality for a doctor to diagnosis can not be obtained, the diagnostic image may be photographed again. It is noted that the diagnostic image that has passed the QA process is also called a "checked diagnostic image".

The image processing parameters that can be set at a user level, such as a radiographer or a doctor, are roughly classified into GP (gradation processing) parameters, RP (frequency processing) parameter, DRC (dynamic range compressed processing) parameters, and TAS (linear tomographic fault shade removal processing) parameters. Each of the image processing parameters is detailed below.

TABLE 1

GP (Gradation Processing) Parameters

| Parameter | Properties | Input Range |
|---|---|---|
| GA | The tendency of the gradation curve. It adjusts the contrast of the image. | −4.0~−0.1 0.1~4.0 |
| GT | Figure of the gradation curve. It has the same effect as the changing of the γ curve of several kind of X ray film. | A~Z |
| GC | A central density of the tendency of the gradation curve. It changes GA centering around GC. | 0.30~2.64 |
| GS | A parallel movement of gradation curve. It can adjust the display density of the entire image. | −1.44~1.44 |
| S-Shift | A coefficient relating to the original sensitivity. It can adjust the display density of the entire image. | /(÷)2.0 ~(×)2.0 |
| C-Shift | A coefficient relating to GA. It can adjust the contrast of the entire image. | (×)0.5~2.0 |

TABLE 2

RP (Frequency Processing) Parameters

| Parameter | Properties | Input Range |
|---|---|---|
| RN | Emphasized frequency range in frequency processing. | 0~9(10 917″) |
| RT | Figure of the curve in accordance with the density of image. It adjusts the level of emphasis within a predetermined density range. | A~Z |
| RE | Emphasizing density of frequency processing. The Intensity of the process changes in accordance with RE value. | 0.0~9.9 10~16 |

TABLE 3

RP (dynamic range compressed processing) Parameters

| Parameter | Properties | Input Range |
|---|---|---|
| DRN | The mask size of DR compressing. It sets the processing range along with DRT. | 0~9 (10 types) |
| DRT | Type of DR compressing filter. It sets the range to be processed. | A~T (20 types) |
| DRE | The level of DR compress filtering process. The intensity of the process changes in accordance with DRE value. | 0.0~9.9 10~16 |

TABLE 4

TAS (linear tomographic fault shade removal processing) Parameters

| Parameter | Properties | Input Range |
|---|---|---|
| ORN | The mask size of one-dimensional BOKE mask processing. Set the most effective size in accordance with the dislocation angle. | 0~9 (10 types) |
| ORE | The level of emphasis of one-dimensional BOKE mask processing. The intensity of the process changes in accordance with ORE value. | 10~16 |

TABLE 4-continued

TAS (linear tomographic fault shade removal processing) Parameters

| Parameter | Properties | Input Range |
|---|---|---|
| ORD | The direction of one-dimensional BOKE mask processing. Set the direction in accordance with the scanning direction and the track direction of the dislocation. | 0: orthogonal 1: parallel |

The "generated diagnostic images" and "checked diagnostic images" operated by the radiographer may be saved on a local disk in the modality apparatus or may be transferred to the image file server 10C and saved therein. The checked diagnostic images are once stored on the image file server 10C. In other words, the checked diagnostic images are that which are subject to diagnosis, wherein an access right to them is granted to doctors and nurses who prepare for those diagnostic images for doctors.

For example, a doctor retrieves diagnostic images of a predetermined patient on a workstation serving as a diagnostic image viewer 10A in order to make a diagnosis. Upon diagnosis, the doctor may change the image processing parameters (e.g., for dark and light adjustment) of the diagnostic images. The diagnostic image having been diagnosed by the doctor is also called an "observed diagnostic image" herein. The image processing parameters applied to the diagnostic contents and images by a doctor are important medical records, which are saved in the image file server 10C along with the observed diagnostic images.

In each of the processes of generation, check and observation of diagnostic images shown in FIG. 2, the diagnostic image is added various kinds of collateral information, including information of a corresponding patient, an examination date, and examination contents. These kinds of collateral information are important as a medical record along with the corresponding diagnostic images.

Figure 3:
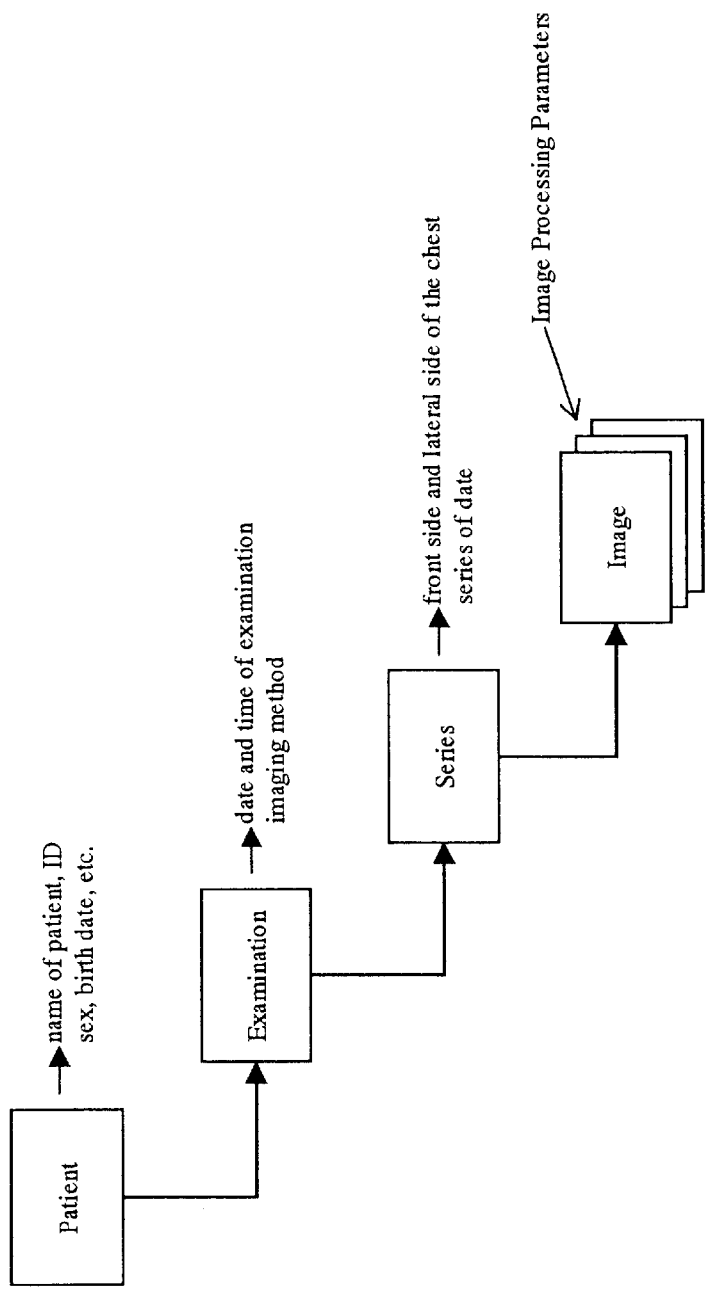
FIG. 3 depicts a structure of a diagnostic image file.

In the embodiment of the present invention, the diagnostic image file is described with being structured as shown in FIG. 3, thus the collateral information can be dealt with concurrently with the corresponding diagnostic image. As shown in FIG. 3, the diagnostic image file comprises a patient field, an examination field, a series field, and an image field.

In the patient field, there is written personal information for identifying a patient corresponding to the diagnostic images or specifying a class, such as a name of patient, an identification number, sex, a birth date, etc.

In the examination field, there are written an examination date when photographs are taken, time, an imaging method (e.g., simple imaging of inner chest), etc.

In the series field, there are written a series of dates and time when the affected parts, such as the front side and lateral side of the chest, have been photographed in sequence.

One image file can contain one or more frames of image data. The image processing parameters applied to each image data (e.g., direction of image) may be saved in conjunction with the image data. In addition, the image data having been observed by a doctor may be added tag information showing an "observed diagnostic image".

In a network system according to the embodiment of the present invention, the image file server 10C permanently archives the diagnostic images automatically on a removable medium in response to a request from clients, thereby averting the risk of involuntarily deleting important diagnostic images as well as saving the operators the trouble of storage operations. In the specification, a client means an radiographic technician who manipulates as an operator a modality apparatus 50 that generates images, or a doctor who observes the diagnostic images on an image viewer 10A by applying the image processing parameters of the observing images. Hereinafter, it will be described about an automatic storage function of diagnostic images performed by the image file server 10C.

Figure 4:
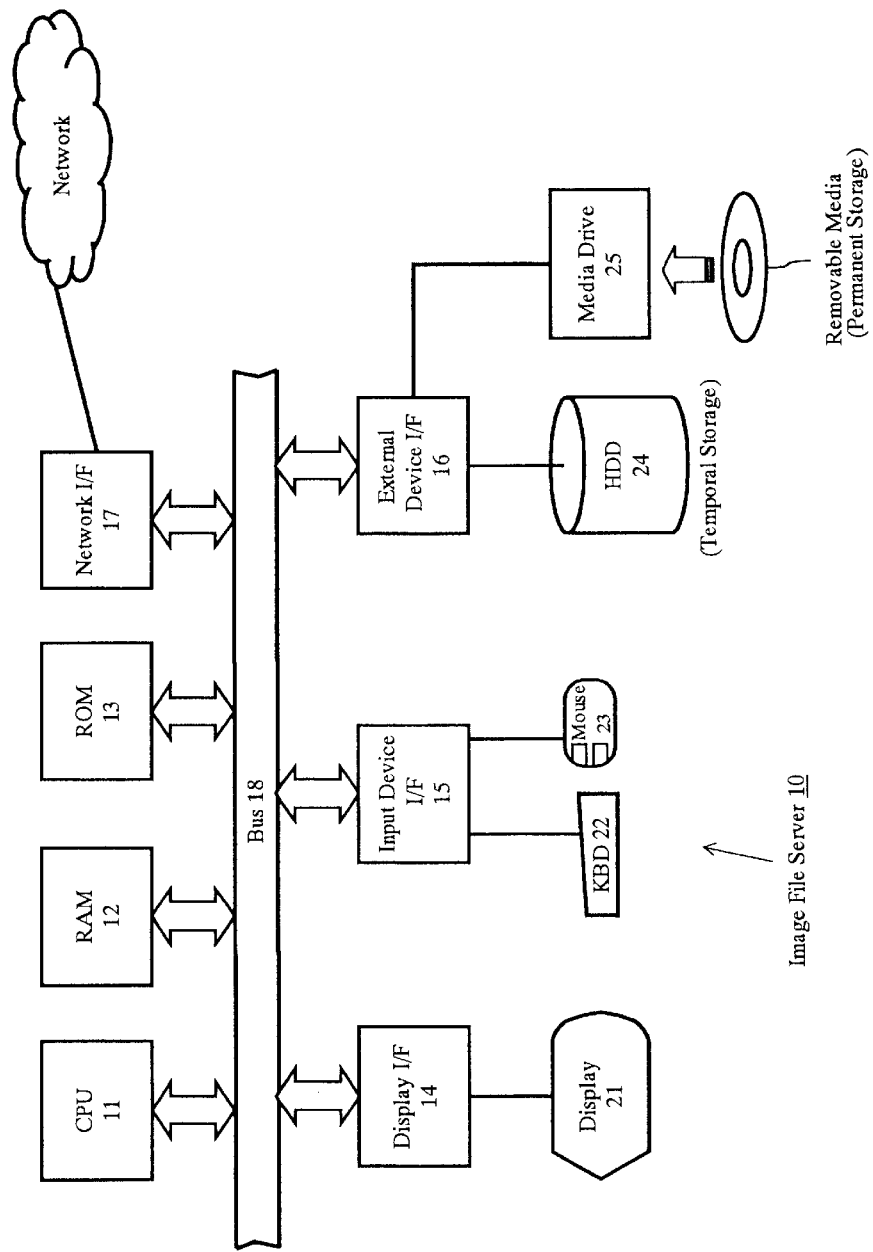
FIG. 4 depicts a hardware configuration of image file server 10C.

FIG. 4 depicts a hardware configuration of image file server 10C. Image file server 10C is practically embodied by activating a predetermined server application on a typical computer system called workstation (WS) or personal computer (PC). An example of the computer system is an IBM PC/AT (Personal Computer/Advanced Technology) compatible machine or its successor machine. Hereinafter each part of server system 10C will be described.

A CPU (Central Processing Unit) 11 serving as a main controller of the system 10C performs various kinds of applications under the control of the operating system (OS).

As shown in FIG. 4, CPU 11 is interconnected to other devices (described below) via a bus 18. Each of the devices on bus 18 is granted a unique memory address or I/O address, thus CPU 11 can access each of the devices connected to bus 18 by addressing. Bus 18 is a common signal transmission path including an address bus, data bus and control bus, an example of which is PCI (Peripheral Component Interconnection) bus.

RAM 12 is a volatile memory device used to store a program code executed in CPU 11 or temporarily store work data under execution. ROM 13 is a nonvolatile memory device for permanently storing a program code or data, in which BIOS (Basic Input/Output System) or POST (Power on Self Test Program) are stored, for example.

Display interface 14 is a peripheral device for actually processing drawing instructions issued by CPU 11. Drawing data processed in display interface 14 is output to display 21 after once written to a frame buffer (not shown), for example. Display 21 may be a CRT (Cathode Ray Tube), for example.

Input device interface 15 is a device for connecting user input devices, such as a keyboard 22 and mouse 23, to the system 10.

Network interface 17 connects system 10 to a network (not shown) such as a LAN (Local Area Network) according to a predetermined communication protocol such as Ethernet. Network interface 17 is typically provided in the form of LAN adapter card, which is installed into a PCI bus slot on the system board (not shown).

Multiple host computers are connected transparently on the LAN to construct a distributed computing environment. Furthermore, some of the host computers operate as a router to interconnect to other LANS, the intranet, and some other external wide area network such as the Internet.

External device interface 16 is a device for connecting external devices such as hard disk drive (HDD) 24 and media drive 25 to system 10C. External device interface 16 complies with an interface standard such as IDE (Integrated Drive Electronics) and SCSI (Small Computer System Interface).

HDD 24 is an external storage device loading a magnetic disk fixedly as a storage medium and is superior to other external storage devices in terms of storage capacity and data transfer rate. It is noted that placing a software program on HDD 24 in an executable condition is called "installing" a program in a system. Typically, on HDD 24 are stored a program code of the operating system executed by processor 11, application programs, and device drivers in a nonvolatile condition. For example, a server application according to the present invention can be installed on HDD 24. Furthermore, HDD 24 is used to temporarily store the diagnostic image files sent from external devices such as modality apparatuses and image viewers.

Media drive 25 is a device for loading removable media such as a CD (Compact Disk), MO (Magneto-Optical Disk) and DVD (Digital Versatile Disk) and accessing their recording surface. The removable media is mainly used to back up software programs and data files in a computer-readable format or to move (including sales, logistics, and distribution) them among multiple systems.

In the embodiment of the invention, the removable media are used as a permanent storage for diagnostic image files. Though the storage capacity of one piece of removable medium is finite, replacing the medium on the media drive 25 provides nearly inexhaustible storage capacity.

Figure 5:
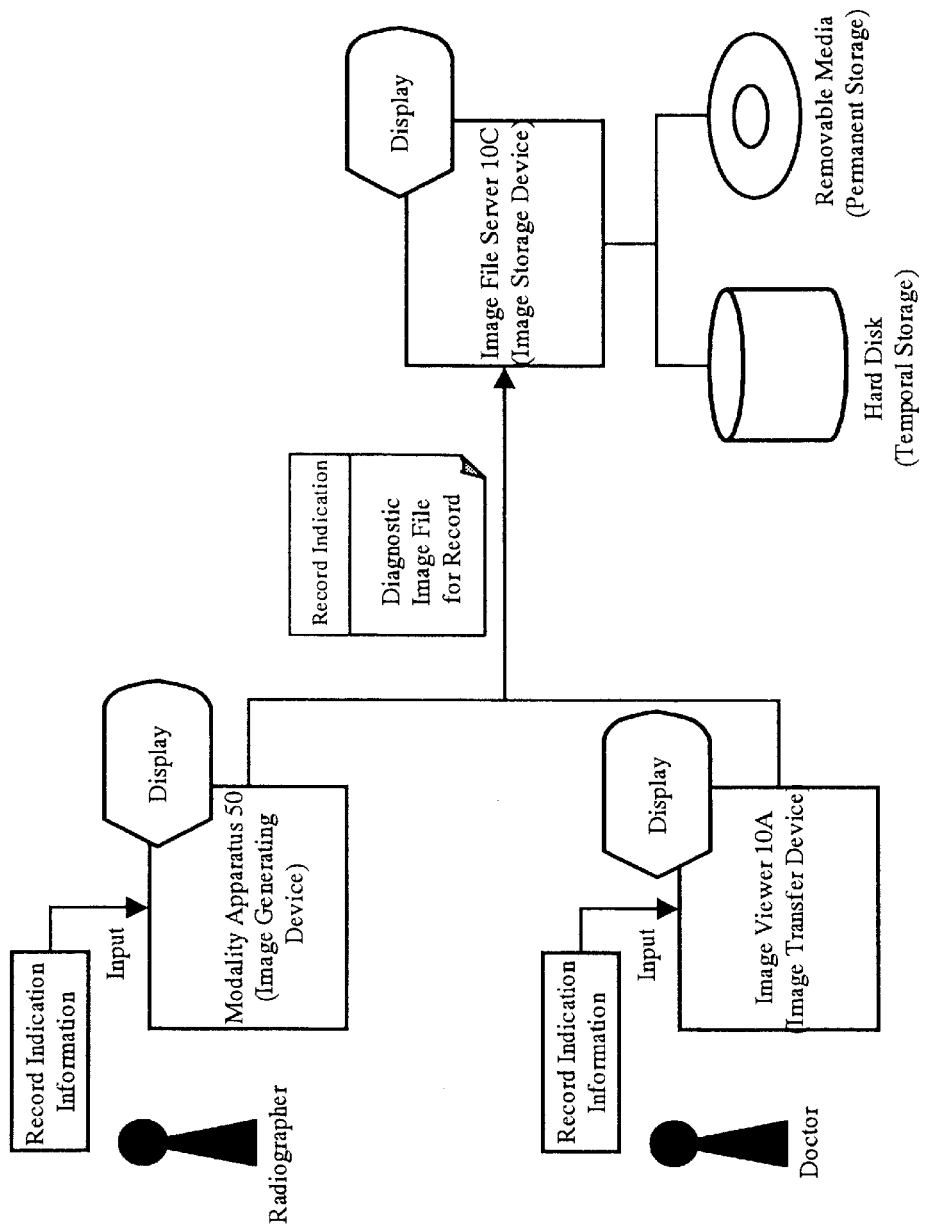
FIG. 5 is a diagram illustrating automatic storage processing of image information performed on image file server 10C.

Next, with reference to FIG. 5, it will be described about automatic storage processing of image information performed between the image file server 10C and external devices such as modality apparatuses 50 and image viewer 10A.

Image file server 10C, which serves as an image storage device for storing diagnostic image files, is interconnected via the network with each of the modality apparatuses 50 serving as image generation devices and image viewer 10A serving as an image transfer device.

Modality apparatuses 50 are operated by specialized technicians (e.g., radiographer) to photograph the diagnostic images, properly photograph again, and perform check operations. On the other hand, A doctor who observes the diagnostic images for diagnosis manipulates image viewer 10A, accordingly the diagnostic contents and results are written to the diagnostic image files. The diagnostic images viewed on image viewer 10A may be directly sent from modality apparatuses 50 or may be sent from image file server 10C that temporarily stores them.

Image file server 10C provides a hard disk and removable media as a storage place of diagnostic image files. The hard disk is mainly used to temporarily store the diagnostic image files transferred from modality apparatuses 50 and image viewer 10A, while the removable media are used to permanently archive the diagnostic image files.

Modality apparatuses 50 and image viewer 10A, which are a sender of diagnostic image files, send them with adding record indication information that specifies a medium used for recording. According to this record indication information, image file server 10C either temporarily stores the diagnostic image files on the hard disk or permanently archives them on the removable medium.

Figure 6:
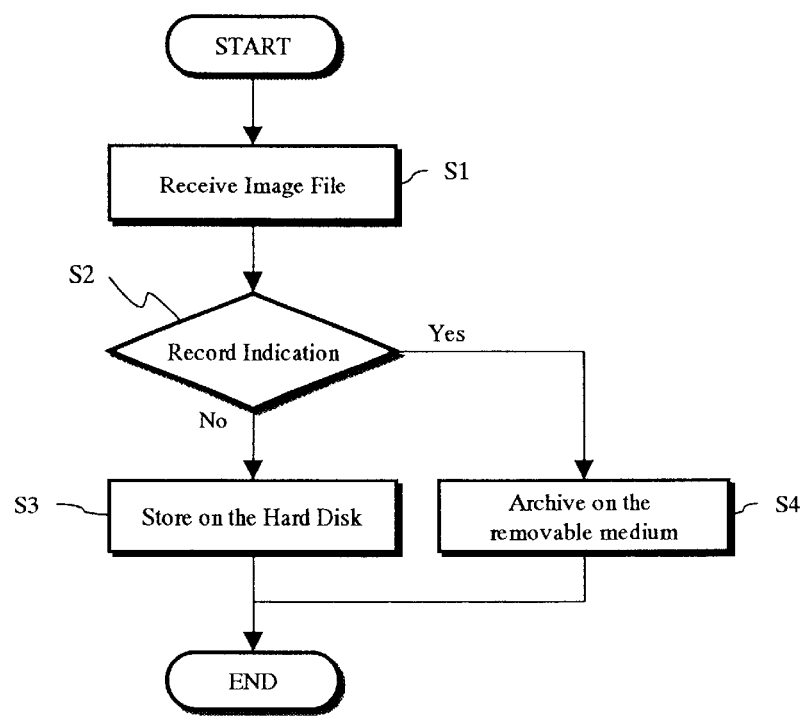
FIG. 6 is a flowchart showing an example of diagnostic image file storing procedure performed on image file server 10C.

FIG. 6 is a flowchart showing an example of diagnostic image file storing procedure performed on image file server 10C.

When image file server 10C receives the diagnostic image file (step S1), it checks the record indication information attached to it (step S2).

If permanent archiving of the diagnostic image file is indicated, it is archived on the removable medium (step S4), and then the routine is ended on the other hand, if permanent archiving is not indicated, the diagnostic image file is temporarily stored on the hard disk (step S3), and then this routine is ended.

Figure 7:
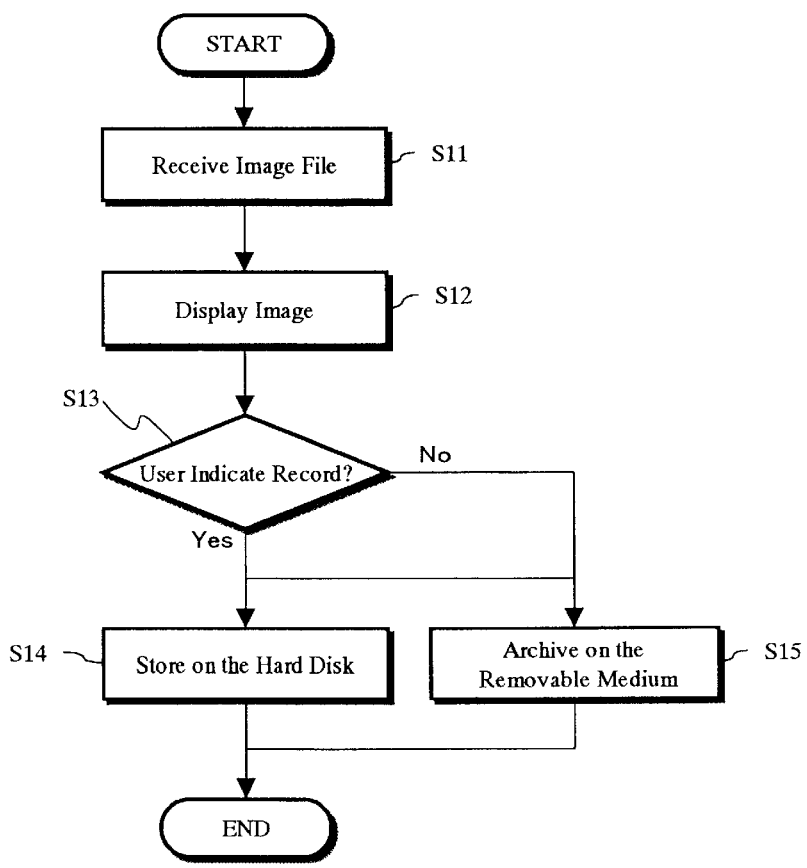
FIG. 7 is a flowchart showing another example of diagnostic image file storing procedure performed on image file server 10C.

FIG. 7 is a flowchart showing another example of diagnostic image file storing procedure performed on image file server 10C.

When image file server 10C receives the diagnostic image file (step S11), it displays this image file on the display screen (step S12).

Then, image file server 10C determines while displaying whether a user inputs a record indication within a certain period of time (step S13). If no indication has been made from the user, this diagnostic image file is archived on the removable medium, thereby preventing involuntary data deletion (step S15). Displaying the diagnostic image on the image viewer corresponds to observation and interpretation by a doctor, thus the important medical data is automatically retained by means of such processing.

On the other hand, if a record indication has been made from the user, the diagnostic image file is either temporarily stored on the hard disk or permanently archived on the removable medium according to the indication (steps S14, S15).

As an alternate approach for the procedure shown in FIG. 7, if no record indication has been made from the user within a certain period of time while displaying the diagnostic image on image viewer 10A, the diagnostic image file may be temporarily stored on the hard disk as well as a reservation for permanent archiving may be made in order to prevent involuntary data deletion.

Figure 8:
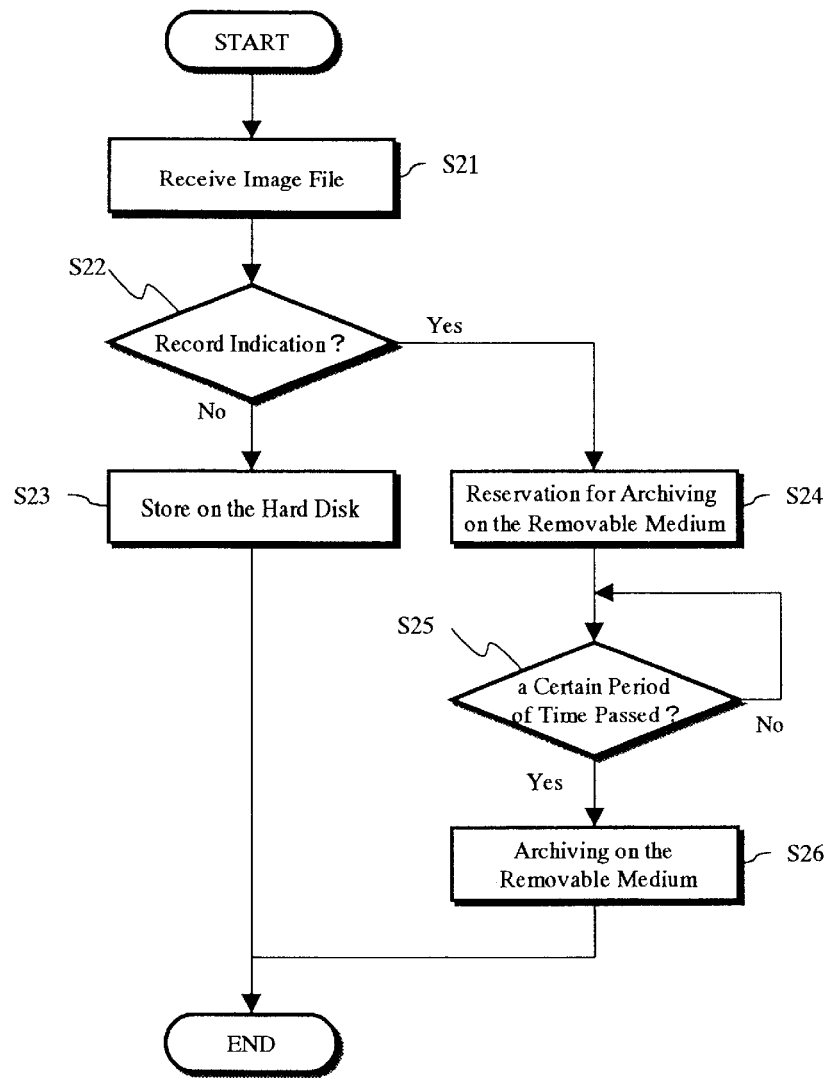
FIG. 8 is a flowchart showing a further example of diagnostic image file storing procedure performed on image file server 10C.

FIG. 8 is a flowchart showing a further example of diagnostic image file storing procedure performed on image file server 10C.

When image file server 10C receives the diagnostic image file (step S21), it checks the record indication information attached to it (step S22).

If permanent archiving is not indicated, the diagnostic image file is temporarily stored on the hard disk (step S23), and then the routine is ended.

On the other hand, if a reservation for permanent archiving of the diagnostic image file is indicated, it is temporarily stored on the hard disk in a condition where a reservation for permanent archiving is made (step S24). Thereafter, when a certain period of time has passed, the diagnostic image file is to be permanently archived on the removable medium (step S26).

Figure 9:
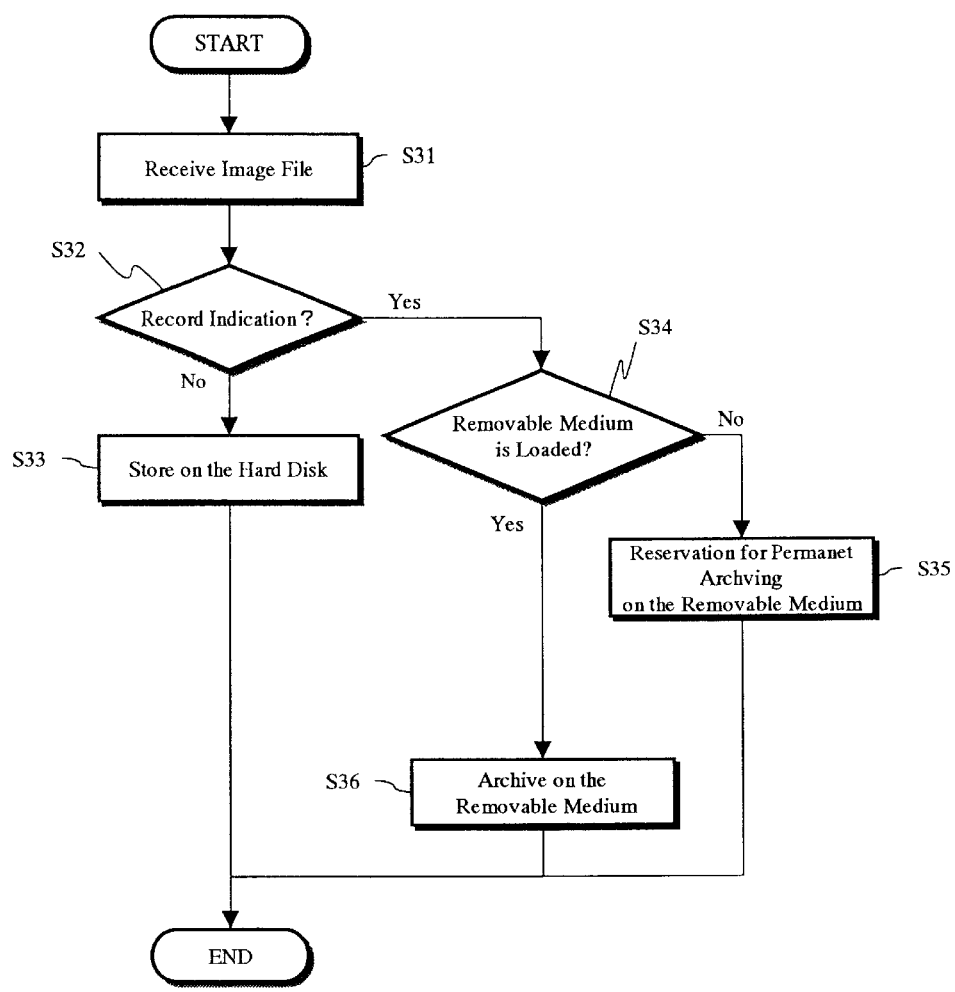
FIG. 9 is a flowchart showing a still further example of diagnostic image file storing procedure performed on image file server 10C.

FIG. 9 is a flowchart showing a still further example of diagnostic image file storing procedure performed on image file server 10C.

When image file server 10C receives the diagnostic image file (step S31), it checks the record indication information attached to it (step S32).

If permanent archiving is not indicated, the diagnostic image file is temporarily stored on the hard disk (step S33), and then the routine is ended.

On the other hand, if permanent archiving of the diagnostic image file is indicated, it is determined whether a removable medium serving as a permanent storage is loaded in the media drive 25 (or whether an enough free capacity exists in the removable medium currently loaded) (step S34).

If the removable medium serving as a permanent storage of the diagnostic image file is loaded in the media drive25 (or an enough free capacity exists in the removable medium currently loaded), the diagnostic image file is permanently archived on the removable medium (step S36), and then the routine is ended.

On the other hand, if the removable medium is not loaded (or an enough free capacity does not exist in the removable medium currently loaded), a reservation is made for permanent archiving on the removable medium (step S35). When the reservation for permanent archiving is made like this, the diagnostic image file is temporarily stored on the hard disk. Thereafter, when the current removable medium is replaced with a new one, it will be archived thereon.

Figure 10:
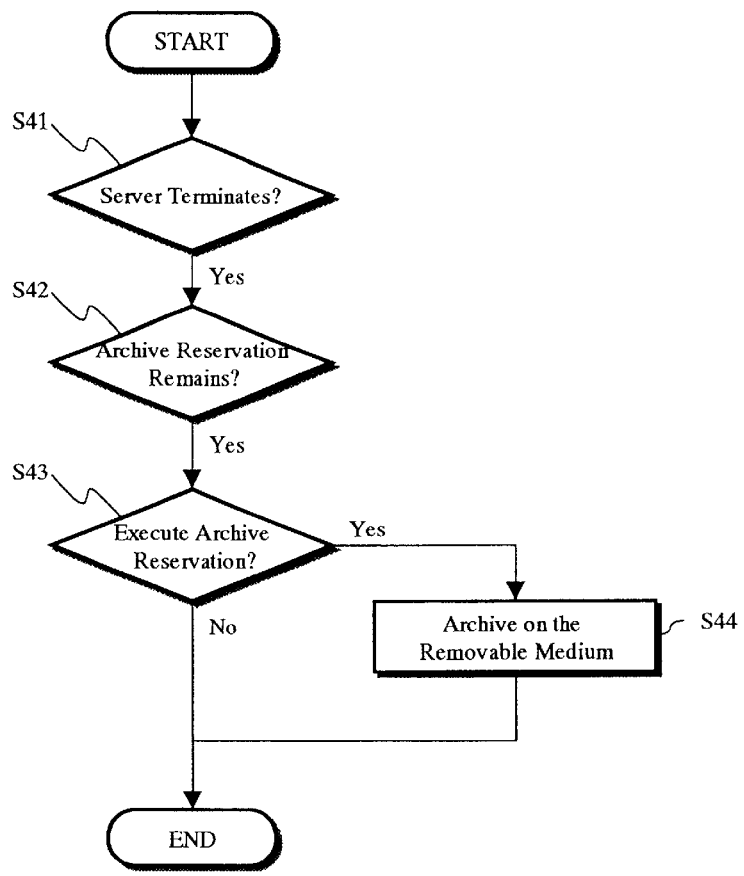
FIG. 10 is a flowchart showing a yet further example of diagnostic image file storing procedure performed on image file server 10C.

FIG. 10 is a flowchart showing a yet further example of diagnostic image file storing procedure performed on image file server 10C.

When image file server 10C is terminated (step S41), it is determined whether the diagnostic image file with permanent archiving reserved remains in the hard disk without being permanently archived (step S42).

If there remains the untreated reservation for permanent archiving, it is queried to a user whether or not to permanently archive the diagnostic image on the removable medium before terminating the image file server 10C (step S43). For example, a dialog for prompting a user's determination may be displayed on the display screen.

When the user desires permanent archiving, the diagnostic image file is archived on the removable medium (step S44) before terminating the system. On the other hand, if the user does not desire permanent archiving, the system is terminated without archiving on the removable medium.

Figure 11:
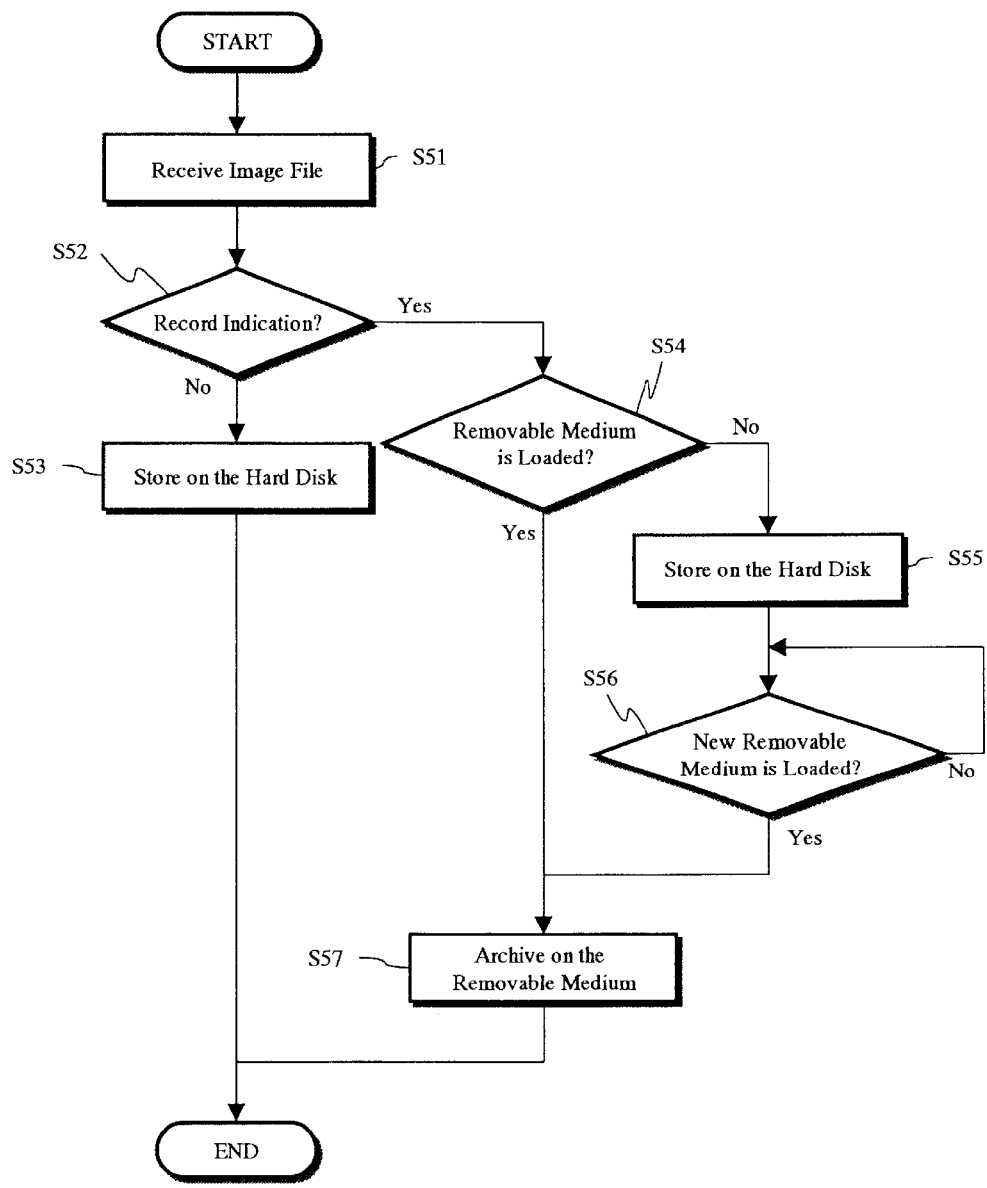
FIG. 11 is a flowchart showing yet another example of diagnostic image file storing procedure performed on image file server 10C.

FIG. 11 is a flowchart showing yet another example of diagnostic image file storing procedure performed on image file server 10C.

When image file server 10C receives the diagnostic image file (step S51), it checks the record indication information attached to it (step S52).

If permanent archiving is not indicated, the diagnostic image file is temporarily stored on the hard disk (step S53), and then this routine is ended.

On the other hand, if permanent archiving of the diagnostic image file is indicated, it is determined whether a removable medium serving as a permanent storage is loaded in the media drive 25 (or whether an enough free capacity exists in the removable medium currently loaded) (step S54).

If the removable medium serving as a permanent storage of the diagnostic image file is loaded in the media drive 25 (or an enough free capacity exists in the removable medium currently loaded), the diagnostic image file is permanently archived on the removable medium (step S36), and then this routine is ended.

On the other hand, if the removable medium is not loaded (or an enough free capacity does not exist in the removable medium currently loaded), the diagnostic image file is temporarily stored on the hard disk (step S55). After waiting for a new removable medium to be loaded into the media drive 25 (step S56), the diagnostic image file is permanently archived on that removable medium (step S57).

As mentioned above, according to the present invention, there is provided a great image management system and image management method for appropriately managing diagnostic image data output by various kinds of medical diagnostic image taking apparatuses, such as a CT (Computed Tomography) apparatus, MR (Magnetic Resonance) apparatus and CR (Computed Radiography) apparatus, by way of a network.

Furthermore, there is provided a great image management system and image management method for automatically retaining necessary diagnostic image files without relying on manual operations and thereby averting the risk of involuntary data deletion.

In addition, according to the image management system and image management method of the invention, it becomes possible to avert the risk of involuntarily deleting important diagnostic images as well as to save the operators the trouble of storage operations by recording the taken images automatically on the storage media.

The present invention has been described with reference to the specific embodiments. However, in view of this disclosure, it will be apparent to those skilled in the art that numerous changes and modifications can be made without departing from the scope and spirit of the invention. Namely, the disclosed invention is to be considered merely as illustrative. In order to judge the summary of the invention, the scope of the claims described at the beginning should be considered.

I claim:

1. An image management system for managing image files on a network, comprising:
    a network interface receiving the image files from one or more users via the network;
    a first image storage temporarily storing the image files;
    a second image storage permanently archiving the image files; and
    a controller controlling storage operations of the image files received via the network, wherein:
    the users can attach a record indication information to the image files;
    the controller checks the record indication information attached to the image files; temporarily stores the image files with permanent-archiving-indication in the first image storage in a condition where a reservation for permanent archiving is made, and then permanently archives the image files in the second image storage after a time period has passed since the image files were temporarily stored in the first image storage.

2. The system of claim 1, wherein the record indication information for determining storage of the image file to the first or second image storage is attached to the image file prior to the image file being transmitted over the network.

3. The system of claim 2 including image modality devices attached to the network, said record indication being provided by one of the image modality devices.

4. An image management system for managing image files on a network, comprising:
    a network interface receiving the image files from one or more users via the network;
    a first image storage temporarily storing the image files;
    a second image storage permanently archiving the image files on a removable medium; and
    a controller controlling storage operations of the image files received via the network, wherein:
    in response to a fact that the removable medium is not loaded in the second image storage or an enough free capacity does not exist in a loaded removable medium currently loaded just when an image file with the permanent-archiving-indication is received, the controller temporarily stores the image file in the first image storage in a condition where a reservation for permanent archiving is made.

5. The image management system according to claim 4, wherein:
    in response to loading of a new removable medium into the second image storage, the controller permanently archives the image file temporarily stored in the first image storage in a condition where a reservation for permanent archiving is made on the removable medium.

6. An image management system for managing image files on a network, comprising:
    a network interface receiving the image files from one or more users via the network;
    a first image storage temporarily storing the image files;
    a second image storage permanently archiving the image files; and
    a controller controlling storage operations of the image files received via the network, wherein:
    upon termination of the system, the controller checks whether an image file in a condition where a reservation for permanent archiving is made is temporarily stored in the first image storage, and if such file is found, queries the one or more users whether or not to archive the image file permanently and then performs any processing in accordance with a user instruction responsive to the query before terminating the system.

7. An image management method for managing image files on a network, comprising:
    receiving an image file with a record indication information attached via the network;
    checking the record indication information attached to the image file;
    temporarily storing the image file with a permanent-archiving-indication in a condition where a reservation for permanent archiving is made; and
    permanently archiving the image file after a time period has passed since the image file was temporarily stored in a condition where a reservation for permanent archiving is made.

8. The method of claim 7, further including forming said image file by modality device and attaching the record indication to the image file prior to receiving the image file via the network.

9. An image management method for managing image files on a network, comprising:
    receiving an image file with a record indication information attached via the network; determining whether a removable medium for permanent archiving is loaded or enough free capacity exists in the loaded removable medium when the image file with the permanent-archiving-indication is received; and
    in response to the absence of the removable medium or a shortage of the free capacity, temporarily storing the image file in the first image storage in a condition where a reservation for permanent archiving is made.

10. An image management method for managing image files on a network, comprising:
    receiving an image file with a record indication information attached via the network;
    upon termination of the system, checking whether an image file in a condition where a reservation for permanent archiving is made is temporarily stored;
    if the image file in the condition where the reservation for permanent archiving is made is temporarily stored, querying a user whether or not to archive the image file having the reservation for permanent archiving permanently; and
    performing any processing in accordance with a user instruction responsive to the query before terminating the system.

11. The image management method according to claim 9, comprising:
    in response to loading of a new removable medium, permanently archiving the image file temporarily stored in a condition where a reservation for with permanent archiving is made on the removable medium.

* * * * *